US006350578B1

(12) United States Patent
Stark et al.

(10) Patent No.: US 6,350,578 B1
(45) Date of Patent: Feb. 26, 2002

(54) METHOD OF QUANTITATING DSDNA

(75) Inventors: Peter C. Stark; Cheryl R. Kuske; Kenneth I. Mullen, all of Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/602,523

(22) Filed: Jun. 23, 2000

Related U.S. Application Data

(60) Provisional application No. 60/141,190, filed on Jun. 25, 1999.

(51) Int. Cl.$^7$ .......................... C12Q 1/68; G01N 33/53; G01N 33/554; G01N 33/00; C07H 21/02
(52) U.S. Cl. ........................... 435/6; 435/7.2; 435/7.32; 435/91.1; 436/94; 536/23.1
(58) Field of Search .......................... 435/6, 91.1, 91.2, 435/183, 91.51, 463, 455, 69.1, 7.2, 7.32; 436/94; 536/23.1, 24.3, 24.33, 25.3

(56) References Cited

U.S. PATENT DOCUMENTS

| 5,436,134 A | 7/1995 | Haugland et al. .............. 435/34 |
| 5,824,557 A | 10/1998 | Burke et al. ................... 436/94 |
| 5,863,753 A | 1/1999 | Haugland et al. .............. 435/34 |

OTHER PUBLICATIONS

Kuske et al., Small–scale DNA sample preparation method to field PCR detection of microbial cells and spores in soil App Environ. Microbiol. 64, 2463–2472, Jul. 1998.*
Cheryl R. Kuske, Kaysie L. Banton, Dante L. Adorada, Peter C. Stark, Karen Hill, and Paul J. Jackson "Small–Scale DNA Sample Preparation Method for Field PCR Detection of Microbial Cells and Spores in Soil," Appl. And Environ. Microbiol., vol. 64, No. 7, Jul. 1998, p. 2463–2472.
R.A. Sandaa, O. Enger, and V. Torsvik, "Rapid Method for Fluorometric Quantification of DNA in Soil," Soil Biol Biochem., vol. 30, No. 2, 1998 p. 265–268.
Andrew Ogram, Gary S. Sayler, and Tamar Barkay, "The Extraction and Purification of Microbial DNA from Sediments," J. Microb. Methods, vol. 7, 1987, p. 57–66.
Robert J. Steffan, Jostein Goksoyr, Asim K, Bej, and Ronald M. Atlas, "Recovery of DNA from Soils and Sediments", Appl. Environ. Microb., vol. 54, No. 12, Dec. 1988, p. 2908–2915.
Asim K. Bej, Meena H. Mahbubani, and Ronald M. Atlas, "Amplification of Nucleic Acids by Polymerase Chain Reaction (PCR) and Other Methods and Their Applications," Crit. Rev. Biochem. and Molec. Biol., vol. 26, 1991, p. 301–334.
Yu–Li Tsai and Betty H. Olson, "Detection of Low Numbers of Bacterial Cells in Soils and Sediments by Polymerase Chain Reaction," Appl. Environ, Microbiol., vol. 58, No. 2, Feb. 1992, p. 754–757.

Alexander N. Glazer and Hays S. Rye, "Stable dye–DNA Intercalation Complexes as Reagents for High–Sensitivity Fluorescence Detection," Nature, vol. 359, Oct. 1992, p. 859–861.
Christoph C. Tebbe and Wilfried Vahjen, "Interference of Humic Acids and DNA Extracted Directly from Soil in Detection and Transformation of Recombinant DNA from Bacteria and a Yeast," Appl. Environ. Microbiol, vol. 59, No. 8, Aug. 1993, p. 2657–2665.
Hays S. Rye, Jonathan M. Dabora, Mark A. Quesada, Richard A. Mathies, and Alexander N. Glazer, "Fluorometric Assay Using Dimeric Dyes for Double– and Single–Stranded DNA and RNA with Picogram Sensitivity," Analyt. Biochem., vol 208, 1993, p. 144–150.
Yu–Li Tsai and Betty Olson, "Rapid Method for Separation of Bacterial DNA from Humic Substances in Sediments for Polmerase Chain Reaction," Appl. Envion. Microbio., vol. 58, No. 7, Jul. 1992, p. 2292–2295.
K. Smalla, N. Cresswell, L. C. Mendonca–Hagler A. Wolters, and J. D. van Elsas "Rapid DNA Extraction Protocol From Soil for Polymerase Chain Reaction–Mediated Amplification," J. Appl. Bact. vol. 74, 1993, p. 78–85.

(List continued on next page.)

Primary Examiner—Ethan C. Whisenant
Assistant Examiner—Frank W Lu
(74) Attorney, Agent, or Firm—Samuel L. Borkowsky

(57) ABSTRACT

A method for quantitating dsDNA in an aqueous sample solution containing an unknown amount of dsDNA. A first aqueous test solution containing a known amount of a fluorescent dye-dsDNA complex and at least one fluorescence-attenutating contaminant is prepared. The fluorescence intensity of the test solution is measured. The first test solution is diluted by a known amount to provide a second test solution having a known concentration of dsDNA. The fluorescence intensity of the second test solution is measured. Additional diluted test solutions are similarly prepared until a sufficiently dilute test solution having a known amount of dsDNA is prepared that has a fluorescence intensity that is not attenuated upon further dilution. The value of the maximum absorbance of this solution between 200–900 nanometers (nm), referred to herein as the threshold absorbance, is measured. A sample solution having an unknown amount of dsDNA and an absorbance identical to that of the sufficiently dilute test solution at the same chosen wavelength is prepared. Dye is then added to the sample solution to form the fluorescent dye-dsDNA-complex, after which the fluorescence intensity of the sample solution is measured and the quantity of dsDNA in the sample solution is determined. Once the threshold absorbance of a sample solution obtained from a particular environment has been determined, any similarly prepared sample solution taken from a similar environment and having the same value for the threshold absorbance can be quantified for dsDNA by adding a large excess of dye to the sample solution and measuring its fluorescence intensity.

10 Claims, No Drawings

OTHER PUBLICATIONS

L. Arlene Porteous, John L. Armstrong, Ramon J. Seidler, and Lidia S. Watrud, "An Effective Method to Extract DNA from Environmental Samples for Polymerase Chain Reaction Amplification and DNA Fingerprint Analysis", Curr. Microb., vol. 29, 1994, p. 301–307.

Jizhong Zhou, May Ann Bruns, and James M. Tiedje, "DNA Recovery from Soils of Diverse Composition," Appl. Environ. Microb., vol. 62, No. 2, Feb. 1996, p. 316–322.

Dominique Marie, Daniel Vaulot, and Frederic Partensky, "Application of the Novel Nucleic Acid Dyes YOYO–1, YO–PRO–1, and PicoGreen for Flow Cytometric Analysis of Marine Prokaryotes," Appl. Environ. Microb., vol. 62, No. 5, May 1996, p. 1649–1655.

Susan J. Ahn, Jose Costa, and Janet Rettig Emanuel "PicoGreen Quantitation of DNA: Effective Evaluation of Samples Pre– or Post–PCR," Nucleic Acids Res., vol. 24, No. 13, 1996, p. 2623–2625.

Victoria L. Singer, Laurie J. Jones, Stephen T. Yue, and Richard P. Haugland, "Characterization of PicoGreen Reagent and Development of a Fluorescence–Based Solution Assay for Double–Stranded DNA Quantitation," Anal. Biochem., vol. 249, 1997, p. 228–238.

* cited by examiner

METHOD OF QUANTITATING DSDNA

STATEMENT REGARDING CROSS-REFERENCES TO RELATED APPLICATIONS

This non-provisional application is based upon and claims the priority of provisional application no. 60/141,190 filed on Jun. 25, 1999, which is hereby incorporated by reference.

This invention was made with government support under Contract No. W-7405-ENG-36 awarded by the U.S. Department of Energy to The Regents of the University of California. The government has certain rights in the invention.

FIELD OF THE INVENTION

The present invention relates generally to a method for quantitating dsDNA in a buffered solution, and more particularly to a method of determining a dilution factor for fluorometric quantitation of dsDNA in solution.

BACKGROUND OF THE INVENTION

The quantitation of dsDNA in a sample may be required for prescreening purposes during DNA typing analysis, for analysis of microorganisms in environmental samples during forensic investigations, for detecting pathogens in food and food crops, for biological warfare agent detection, and for other important applications. Efficient methods for selectively quantitating double stranded DNA (dsDNA) are required for a thorough analysis of cells and microorganisms from the body, from marine environments such as the ocean and the seas, from plant environments such as soil and sediment, etc.

Various methods are used to extract dsDNA from these environments. One strategy involves separating cells or microorganisms from a sample taken from a particular environment, and then lysing the cells to release dsDNA. Another strategy involves lysing the cells or microorganisms in a sample that includes the environmental matrix they have been taken from, and then separating the dsDNA from the matrix. Lysing procedures can include incubating the sample with a detergent, freeze thawing the sample, homogenizing the sample in bead mill, and other steps that rupture the cell wall or cell membrane to release the enclosed dsdNA. Extraction procedures typically provide only small amounts of dsDNA. However, the extracted dsDNA can be amplified by PCR (polymerase chain reaction), a method that uses extracted strands of dsDNA as templates from which exact dsDNA copies are made. This way, an adequate supply of dsDNA is available for analysis. Since dsDNA extracts are generally contaminated with materials that inhibit PCR, adequate removal of these contaminants is required prior to PCR. Soil or sediment extracts, for example, include co-extracted humic acids that can interfere with PCR even if present in very small concentrations.

In addition to the adequate removal of contaminants, the quality and quantity of dsDNA prior to PCR should be known. Solution extracts generally contain proteins that are coextracted with the dsDNA that can interfere with PCR. Spectrophotometric analysis is a commonly used technique to determine the relative amounts of dsDNA and protein in an aqueous extract. In solution, dsDNA has a maximum absorption at a wavelength of 260 nanometers (nm) while proteins absorb light strongly near about 280 nm. After preparing a solution extract, the absorption intensities at 260 nm and 280 nm are recorded, and the $A_{260}/A_{280}$ ratio is calculated to provide an estimate of DNA purity. A ratio of about 1.7–2.0 has been reported to indicate "clean DNA".

Unfortunately, the absorption measurements themselves that are used to obtain this ratio might not reflect the true concentration or purity of dsDNA in the sample solution because nucleotides, single stranded nucleic acids, and other contaminants can also contribute significantly to the absorption signals.

Fluorometric analysis is another method used to quantitate dsDNA in a sample containing dsDNA. It is a highly sensitive method, and involves adding a non-fluorescent dye to a solution containing dsDNA to produce a highly fluorescent dye-dsDNA complex. The fluorescence intensities for a wide range of concentrations of the complex are measured, and these measurements are used to create a standard curve. The dye is added to a solution containing an unknown amount of dsDNA to form the complex. The fluorescence intensity of this solution is measured, and the standard curve is used for comparison to determine the concentration of the complex in the solution. Some of the dyes used have been described in U.S. Pat. No. 5,436,134 to R. P. Haugland entitled "Cyclic-Subsituted Unsymmetrical Cyanine Dyes," and in U.S. Pat. No. 5,863,753 to R. P. Haugland et al. entitled "Chemically Reactive Unsymmetrical Cyanine Dyes and Their Conjugates".

Results of fluorometric analyses must be interpreted carefully since samples prepared for analysis can include contaminants that prevent an accurate quantitation of the dsDNA in the sample. Contaminants such as proteins, for example, can bind to DNA and prevent the dye from forming the dye-dsDNA complex. U.S. Pat. No. 5,824,557 to T. J. Burke entitled "Method for Detecting and Quantitating Nucleic Acid Impurities in Biochemical Preparations," which issued on Oct. 20, 1998, describes a fluorometric analysis method that uses a detergent to prevent proteins from binding to DNA.

Fluorometric analysis of samples prepared form soil or sediment environment is generally contaminated with humic acids that attenuate the measured fluorescence intensity of the dye/dsDNA complex. "Rapid Method for Fluorometric Quantification of DNA in Soil" by R. A. Sandaa et al. which was published in Soil Biol. Biochem, 1998, vol. 30, no. 2, pp. 265–268, includes a description of using fluorometric analysis to quantitate dsDNA from soil extracts. A buffered solution containing dsDNA extracted form soil was combined with PicoGreen dye to form the dye-dsDNA complex. The fluorescence intensity of the solution was measured and compared to standards to determine the concentration of dsDNA in the extract. For insufficiently dilute samples, humic acids present in the extract attenuated the fluorescence of the dye-dsDNA complex. To ensure that a sufficiently dilute sample solution was prepared, a dilution series for each soil sample was required.

Although fluorometric analysis an important technique for quantitating dsDNA in the sample solution, and the quantity of dsDNA in a solution is required knowledge prior to PCR amplification, sample solutions often contain contaminants in amounts sufficient to interfere with fluorescence measurements and with subsequent PCR amplification procedures. A method that accurately and efficiently quantifies dsDNA in the presence of contaminants is therefore highly desirable. In order to avoid time lost in transporting samples to a laboratory to be analyzed, it is also desirable that this method be flexible enough for use in the field where the samples are obtained.

Therefore, an object of the present invention is to provide a method for quantitating dsDNA in the presence of contaminants.

Another object of the invention is to provide a method of accurately quantitating dsDAN in a solution that is contaminated with humic acids.

Still another object of the invention is a method for quantitating dsDNA that can be used in the field.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the present invention includes a method for quantitating dsDNA in an aqueous sample solution containing an unknown amount of dsDNA. A first aqueous test solution containing a known amount of a fluorescent dye-dsDNA complex and at least one fluorescence-attenutating contaminant is prepared. The fluorescence intensity of the test solution is measured. The first test solution is diluted by a known amount to provide a second test solution having a known concentration of dsDNA. The fluorescence intensity of the second test solution is measured. Additional diluted test solutions are similarly prepared until a sufficiently dilute test solution having a known amount of dsDNA is prepared that has a fluorescence intensity that is not attenuated upon further dilution. The value of the maximum absorbance of this solution between 200–900 nanometers (nm), referred to herein as the threshold absorbance, is measured. A sample solution having an unknown amount of dsDNA and an absorbance identical to that of the sufficiently dilute test solution at the same chosen wavelength is prepared. Dye is then added to the sample solution to form the fluorescent dye-dsDNA-complex, after which the fluorescence intensity of the sample solution is measured and the quantity of dsDNA in the sample solution is determined.

Once the threshold absorbance of a sample solution obtained from a particular environment has been determined, any similarly prepared sample solution taken from a similar environment and having the same value for the threshold absorbance can be quantified for dsDNA by adding a large excess of dye to the sample solution and measuring its fluorescence intensity.

DETAILED DESCRIPTION OF THE INVENTION

Briefly, the present invention includes a method for the fluorometric quantitation of dsDNA present in a sample. A test solution having dsDNA and a fluorescence attenuating contaminant present in the sample is prepared. A non-fluorescent dye that binds to dsDNA to form a fluorescent dye-dsDNA complex is added to the solution and the fluorescence is measured. The test solution is diluted and the fluorescence is measured. Additional dilutions and fluorescence measurements are performed until a solution is prepared having a measured fluorescence intensity that is not attenuated by additional dilution of the fluorescent contaminant. The UV/VIS absorbance at the absorbance wavelength maximum for this test solution is measured. After this information has been obtained, a sample solution from a particular environment, such as soil, is prepared such that the sample solution has a maximum absorbance equal to that of the sufficiently dilute test solution. Then, a non-fluorescent die that binds to dsDNA is added to the sample solution. A large excess of the dye is used to ensure that all of the dsDNA binds to the dye to form a dye-dsDNA complex. The fluorescence intensity of the sample solution is then measured. The concentration of dsDNA in the sample can then be determined by comparing the value of the fluorescence intensity to a previously prepared standard curve that provides known fluorescence intensities for known concentrations of the dye-dsDNA complex.

The method was demonstrated by preparing sample solutions from soil and quantitating the dsDNA in these solutions. The solutions were prepared using known dsDNA extraction procedures, and contained humic acids that were coextracted with the dsDNA. Solutions having 1–10 ng/ml of dye-dsDNA complex are attenuated with as little as 5 ppm of humic acids. This attenuation of the fluorescence intensity can be due to the intrinsic fluorescence of the humic acids themselves, which could contribute to an increase in background fluorescence. In addition, humic acids have phenolic groups that are known to interfere with the formation of dye-dsDNA complexes. Furthermore, humic acids can interfere with the fluorescence of the dye-dsDNA complex though quenching, i.e. self-absorption, or by an energy transfer effect.

In order to relate the fluorescence intensity of the sample solution to the concentration of dsDNA in the solution, a standard fluorescence intensity curve was prepared. Test solutions having known concentrations of PicoGreen dye-dsDNA complex were prepared. The fluorescence intensity each of the test solutions was determined. These fluorescence intensities were used to provide the standard curve for determining the concentration of dsDNA in a sample solution having an unknown concentration of dsDNA.

After preparing the standard curve, a buffered test solution containing humic acids and a known concentration of dsDNA was prepared. After PicoGreen dye was added to the test solution to complex all of the dsDNA and form a PicoGreen dye-dsDNA complex, the fluorescence intensity of the solution was measured using a fluorometer with an excitation wavelength of 486 nm and an emission wavelength of 520 nm. The test solution was diluted and the procedure repeated until the measured fluorescence was not attenuated with increasing dilution. The measured UV/VIS absorbance at the absorption maximum between 200–900 nm was determined to be 0.05 for that test solution. We will refer to this number, 0.05, as the threshold absorbance for soil.

After determining the threshold absorbance for soil, sample solutions were prepared by extracting dsDNA from soil using known extraction procedures. The UV/VIS absorption of these sample between 200–900 nm were measured. If a sample solution had a UV/VIS absorbance of 0.05 between 200–900 nm, then PicoGreen was added and the fluorescence intensity was measured. If the UV/VIS of the sample solution was greater than 0.05 between 200–900 nm, the sample solution was diluted until the measured maximum absorbance between 200–900 nm was 0.05, after which the PicoGreen dye was added as before. If the initial sample solution prepared had a UV/VIS absorbance maximum less than 0.05, then another more concentrated sample solution having absorption equal to or greater than 0.05 was prepared from the soil. Although humic acids are likely present in any sample solution derived from soil, a measured absorbance at or below 0.05, the threshold absorbance for soil, between 200–900 nm indicates that if they are present, they do not interfere with the fluorescence measurement.

A sample solution may contain dsDNA obtained by extraction from any cell or microorganism that contains dsDNA. The choice of extraction methods will be based on the types of cells or microorganisms present in the environment for which dsDNA quantitation is desired. The extraction procedures employed to provide extracts to demonstrate the method of the present invention are known to be effective for extracting dsDNA from bacteria and spores, which are commonly found in soil. The details of these procedures now follow. Extracts were prepared from suspensions of the following microorganisms in the indicated concentrations: (a) the gram-negative bacterium Pseudomonas putida mt-2 (about $10^9$ CFU/ml); (b) the gram-positive bacterium bacillus globigii (about $10^8$ endospores/ml); and (c) spores of the fungus Fusarium moniliforme (about $10^7$ conidia/ml). A combination of extraction techniques referred to as "hot detergent treatment," and "bead mill homogenization" were used to extract the dsDNA. Hot detergent treatment involved combining a 0.5 ml portion of 2×TENS buffer with a 0.5-ml cell or spore suspension (1×TENS buffer is 50 mM Tris HCl [pH 8.0], 20 mM EDTA, 100 mM NaCl, 1% sodium dodecyl sulfate (SDS)). The product was mixed, incubated at 70° C. for 10 minutes, mixed again, and reincubated at 70° C. for another 10 minutes. "Bead mill homogenization" included homogenizing the product from hot detergent treatment in a bead mill. A variety of bead sizes were included to disrupt soil colloids and plant tissue (710–1180 $\mu$m-diameter beads), fungal, plant and other eukaryotic cells (425–600-$\mu$m-diameter beads), and bacterial cells (106-$\mu$m-diameter beads). After homogenizing the sample, it was centrifuged to provide a pellet and a supernatent liquid, both of which contained dsDNA. The pellet was suspended in a TE buffer (10 mM Tris HCl [pH 8.0], 1 mM EDTA). The supernatent was collected and stored on ice.

Soil sample solutions were prepared as follows. A soil sample was first filtered though a 2-mm-pore-size screen and mixed well. About 0.5 g of the filtered sample was combined with one ml of TENS buffer in a 2-ml mini-bead beater vial containing 900 mg of a mixture of beads (300 mg each of beads with a diameter of 710–1180 $\mu$m, 425–600 $\mu$m, and 106 $\mu$m). The hot-detergent technique and bead mill homogenization techniques were conducted as described above to produce, after centrifugation, a soil-bead pellet and a supernatent. The bead mill product was washed once with 1-ml of TENS buffer and centrifuged. The wash supernatent was pooled with the original supernatent. Nucleic acids were precipitated by using 1/10 volume of 3 M sodium acetate (pH 5.2) and 2.5 volumes of ethyl alcohol. The pellet containing DNA was suspended in 100–500 $\mu$l of TE buffer or sterile water.

The dsDNA in the aqueous buffered extracts obtained as described above was quantitated as follows. Each extract was diluted 1/500 in 0.1×TAE, and the UV absorbance in the 200–900-nm range of the diluted extract was measured. If the maximum absorbance of the diluted extract was greater than 0.05, dilution was continued until the absorbance was no greater than 0.05. An equal volume of a 200-fold dilution of PicoGreen dye was added to the diluted extract and the resulting mixture was incubated at room temperature in the absence of light for about 10 min. The fluorescence of the mixture was determined using a fluorometer with an excitation wavelength of 486 nm and an emission wavelength of 520 nm. A reference curve was prepared by measuring the fluorescence of various known concentrations of the dye-dsDNA complex. The dsDNA in the extract was quantitated by measuring the fluorescence of the dye-dsDNA complex formed when PicoGreen dye was added to the extract and comparing the measured fluorescence to the standard curve. Although other non-fluorescent dyes that become fluorescent upon complexation with dsDNA are known, PicoGreen dye is preferred.

After the dsDNA in the extract was quantitated as described above, a spin microcolumn was used to remove additional humic acids from the extract to the extent that the remaining humic extracts would not prevent amplification by PCR. After quantitating the dsDNA in the purified extract for reasons related to PCR amplification parameters, dsDNA was then amplified by PCR.

In a laboratory setting, dsDNA quantitation is typically accomplished by agarose gel electrophoresis. However, this is not applicable to field use. The method of the present invention can be used in the field for dsDNA quantitation for crude and purified DNA extracts. The method can be employed using a kit that can be taken into the field. Such a kit includes buffers, detergent, a bead mill, a microcentrifuge, a battery, and a battery-operated device or devices that measure UV/VIS absorption and fluorescence of dsDNA extracts.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for quantitating dsDNA in a sample, comprising the steps of:
   (a) preparing a buffered test solution comprising a fluorescence attenuating material, a known amount of dsDNA, and a dye in an amount sufficient to combine with all of the dsDNA in the test solution to provide a highly fluorescent dye-dsDNA complex;
   (b) measuring the fluorescence intensity of the test solution;
   (c) preparing a diluted test solution from the test solution of step (a) and measuring fluorescence intensity of the diluted test solution;
   (d) repeating step c) until a sufficiently diluted test solution is prepared having a measured fluorescence intensity that is not attenuated upon further dilution;
   (e) measuring the absorbance of the sufficiently diluted test solution of step d);
   (f) preparing a sample solution comprising dsDNA extracted from the sample and having a measured absorbance equal to that of the sufficiently diluted test solution of step e);
   (g) adding the dye to the sample solution in an amount sufficient to combine with all of the dsDNA in the sample solution to provide the dye-dsDNA complex; and
   (h) measuring the fluorescence intensity of the dye containing sample solution of step g).

2. The method of claim 1, where the dye is PicoGreen dye.

3. The method of claim 1, where the absorbance is measured in the ultraviolet-visible region of the electromagnetic spectrum at about 200–900 nm.

4. The method of claim 1, wherein the sample is a soil sample.

5. The method of claim 1, wherein buffered sample solution comprises humic acids.

6. The method of claim 1, further comprising the steps of:
   (a) preparing a standard fluorescence intensity curve comprising a range of concentrations of dye-dsDNA complex, the concentration of the dye-dsDNA complex of the sample solution being within that range; and
   (b) using the standard curve to quantitate the dsDNA in the sample solution.

7. A method for quantitating dsDNA in soil sample comprising the steps of:
   (a) preparing from the soil sample an aqueous buffered solution comprising dsDNA and humic acids extracted from the soil, the solution having an absorbance maximum of about 0.05 in the ultraviolet-visible range of the electromagnetic spectrum between about 200–900 nm.;
   (b) adding a PicoGreen dye to the extract, whereby the dye and dsDNA combine to produce a fluorescent dsDNA-dye complex; and
   (c) measuring the fluorescence of the solution after adding the dye to the solution.

8. The method of claim 7, wherein preparation of the soil sample includes bead mill homogenization.

9. The method of claim 7, wherein said soil sample is subjected to treatment with sodium dodecyl sulfate.

10. The method of claim 7, further comprising the steps of:
   (a) preparing a standard fluorescence intensity curve comprising a range of concentrations of dye-dsDNA complex, the concentration of the dye-dsDNA complex of the sample solution being within that range; and
   (b) using the standard curve to quantitate the dsDNA in the sample solution.

* * * * *